United States Patent
Diaz et al.

(10) Patent No.: US 7,201,768 B2
(45) Date of Patent: Apr. 10, 2007

(54) METHOD AND DEVICE FOR RETRIEVING EMBOLIC COILS

(75) Inventors: Roberto Diaz, Miami, FL (US); Vladimir Mitelberg, Aventura, FL (US)

(73) Assignee: Cordis Neurovascular, Inc., Miami Lakes, FL (US)

(*) Notice: Subject to any disclaimer, the term of this patent is extended or adjusted under 35 U.S.C. 154(b) by 594 days.

(21) Appl. No.: 10/693,246

(22) Filed: Oct. 24, 2003

(65) Prior Publication Data

US 2004/0106932 A1 Jun. 3, 2004

Related U.S. Application Data

(62) Division of application No. 09/865,642, filed on May 25, 2001, now Pat. No. 6,673,100.

(51) Int. Cl.
*A61F 2/06* (2006.01)
(52) U.S. Cl. .............. 623/1.11; 623/2.11; 606/108; 606/191; 606/198; 606/200
(58) Field of Classification Search .............. 623/1, 623/1.17, 1.23, 2.11; 606/108, 127, 128, 606/131, 133, 158, 205, 198, 210, 191
See application file for complete search history.

(56) References Cited

U.S. PATENT DOCUMENTS

| | | |
|---|---|---|
| 724,889 A | 4/1903 | Kochenderfer |
| 4,655,219 A | 4/1987 | Petruzzi |
| 4,923,461 A | 5/1990 | Caspari et al. |
| 4,935,027 A | 6/1990 | Yoon |
| 5,108,406 A | 4/1992 | Lee |
| 5,172,700 A | 12/1992 | Bencini et al. |
| 5,217,450 A | 6/1993 | Pryor et al. |
| 5,222,973 A | 6/1993 | Sharpe et al. |
| 5,235,966 A | 8/1993 | Jamner |
| 5,304,183 A | 4/1994 | Gourlay et al. |
| 5,387,219 A | 2/1995 | Rappe |
| 5,562,678 A | 10/1996 | Booker |

(Continued)

FOREIGN PATENT DOCUMENTS

| | | |
|---|---|---|
| DE | 41 15 136 A1 | 11/1992 |
| DE | 198 10 696 C1 | 5/1999 |

*Primary Examiner*—Lalita M. Hamilton
(74) *Attorney, Agent, or Firm*—Henry W. Collins

(57) ABSTRACT

A method and device are disclosed for retrieving embolic coils used for treating an aneurysm of a patient. The method comprises the steps of providing a wire device that is pushable through a microcatheter and has a flexible distal portion comprising distal collapsible arms with a latch member carried by one of the arms. The microcatheter is introduced into a patient's vessel leading to the aneurysm. The wire device, distal end first, is introduced into the microcatheter whereby the arms collapse while they are within the microcatheter. The distal end of the wire device is pushed through the microcatheter whereby the arms open when they extend out of the distal end of the microcatheter. The latch member is manipulated so that it engages an embolic coil to be retrieved. The latch-engaged embolic coil and wire device are withdrawn through the catheter, whereby the arms become collapsed as the arm is withdrawn through the catheter, securing the latch and the embolic coil.

6 Claims, 2 Drawing Sheets

U.S. PATENT DOCUMENTS

| | | |
|---|---|---|
| 5,782,747 A | 7/1998 | Zimmon |
| 5,810,873 A | 9/1998 | Morales |
| 5,868,754 A | 2/1999 | Levine et al. |
| 5,916,235 A | 6/1999 | Guglielmi |
| 5,935,027 A | 8/1999 | Nashif et al. |
| 6,673,100 B2 | 1/2004 | Diaz et al. |

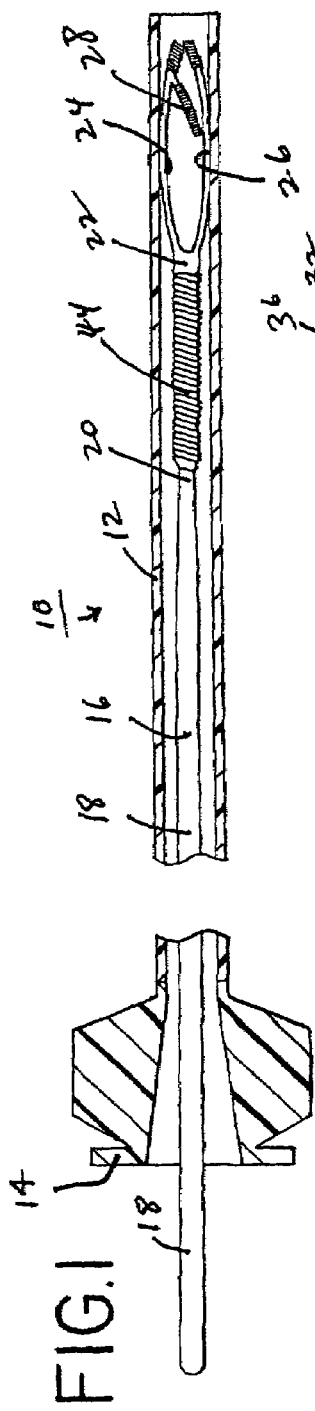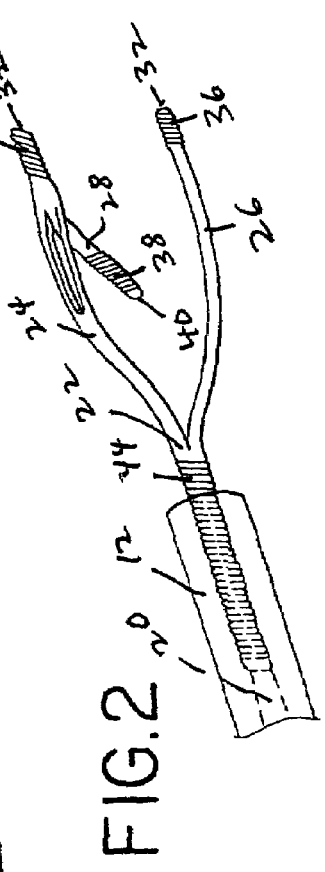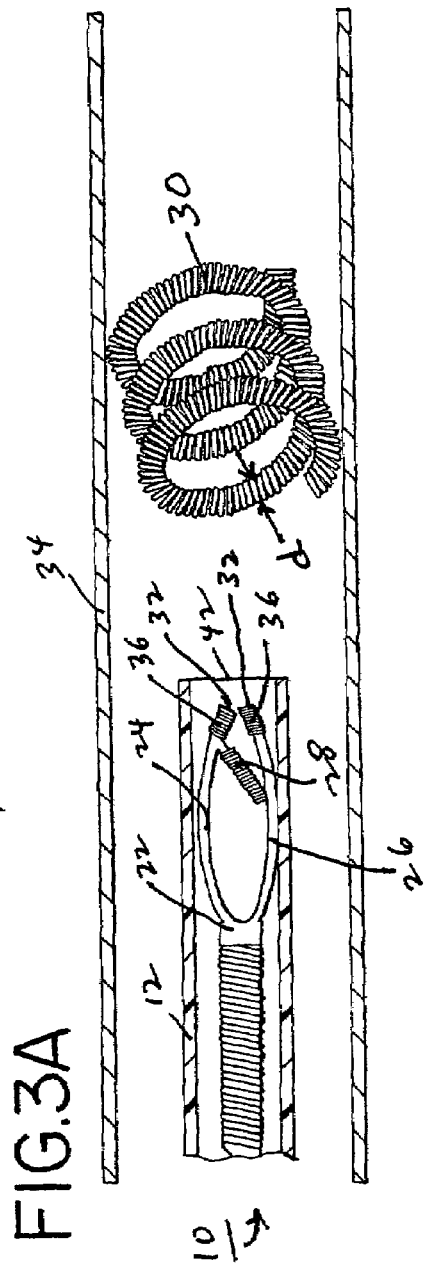

METHOD AND DEVICE FOR RETRIEVING EMBOLIC COILS

This patent application is a divisional patent application of U.S. patent application Ser. No. 09/865,642, filed May 25, 2001.

FIELD OF THE INVENTION

The present invention concerns a novel method and device for retrieving embolic coils used for treating an aneurysm of a patient.

BACKGROUND OF THE INVENTION

A well known method of treating an aneurysm of a vessel wall includes the placement of a number of detachable embolic coils within the aneurysm. Multiple coils are employed during the procedure in an effort to completely embolize the vessel defect. Typically, a deployment device is used to introduce the coils, one by one, via a microcatheter, into the aneurysm. Occasionally during a procedure, an earlier introduced coil may become displaced from the aneurysm and protrude into the parent vessel. This coil protrusion can have a disastrous effect on the patient. Because the embolic coil is in the blood flow, thrombus begins to form around the coil which can potentially occlude the vessel initiating an ischemic attack or the clot may break off, flow distal and occlude other vessels leading to ischemia in another part of the brain. Therefore it is imperative that the misplaced coil be removed.

Certain prior art coil retrieval devices use a loop or snare configuration to try to lasso the misplaced coil. Since the misplaced coil is sometimes a loop, the physician often has difficulty trying to lasso these coils which may add to the procedure time and cause potential complications.

It is, therefore, an object of the invention to provide a novel method for retrieving embolic coils.

It is a further object of the invention to provide a method and device for retrieving embolic coils in which the embolic coils are secured in a retrieval device and prevented from becoming dislodged.

Another object of the present invention is to provide a tool for the physician to enable the physician to rapidly retrieve a misplaced embolic coil.

A further object of the present invention is to provide a pushable wire device for retrieving embolic coils that is simple in operation and relatively easy to manufacture.

Other objects and advantages of the present invention will become apparent as the description proceeds.

SUMMARY OF THE INVENTION

In accordance with the present invention, a method is disclosed for retrieving embolic coils used for treating an aneurysm. The method comprises the steps of providing a wire device that is pushable through a microcatheter and has a flexible distal portion comprising a distal collapsible arm with a latch member carried by the arm. A microcatheter is introduced into a patient's vessel leading to the aneurysm. The wire device is introduced into the microcatheter whereby the arm collapses while it is within the microcatheter. The distal end of the wire device is pushed through the microcatheter whereby the arm opens when it extends out of the distal end of the microcatheter. The latch member is manipulated so that it engages an embolic coil to be retrieved. The latch-engaged embolic coil and the wire device are withdrawn through the catheter whereby the arm becomes collapsed as the arm is withdrawn through the catheter.

In the illustrative embodiment, the flexible distal portion comprises a pair of distal collapsible arms with a latch member carried by at least one of the arms.

In the illustrative embodiment, the wire device has a stiffer proximal portion than the distal portion. A portion of the collapsible arm is radiopaque and the arm and latch are formed from a composition comprising nitinol.

In accordance with the illustrative embodiment, a medical device is provided for retrieving embolic coils implanted in a patient. The medical device of the illustrative embodiment comprises a wire device that is pushable through a microcatheter and has a flexible distal portion comprising a pair of distal collapsible arms with an angled latch member carried by one of the arms.

A more detailed explanation of the invention is provided in the following description and claims, and is illustrated in the accompanying drawings.

BRIEF DESCRIPTION OF THE DRAWINGS

FIG. 1 is a cross sectional view of a microcatheter containing an embolic coil retrieving device according to the principles of the present invention.

FIG. 2 is a perspective view of a distal portion of the embolic coil retrieving device of FIG. 1.

FIG. 3A is a view of a microcatheter positioned adjacent an embolic coil within a patient's vessel, with the arms of the embolic coil retrieval device in a collapsed position within the microcatheter.

DETAILED DESCRIPTION OF THE ILLUSTRATIVE EMBODIMENT

Figure 3B:
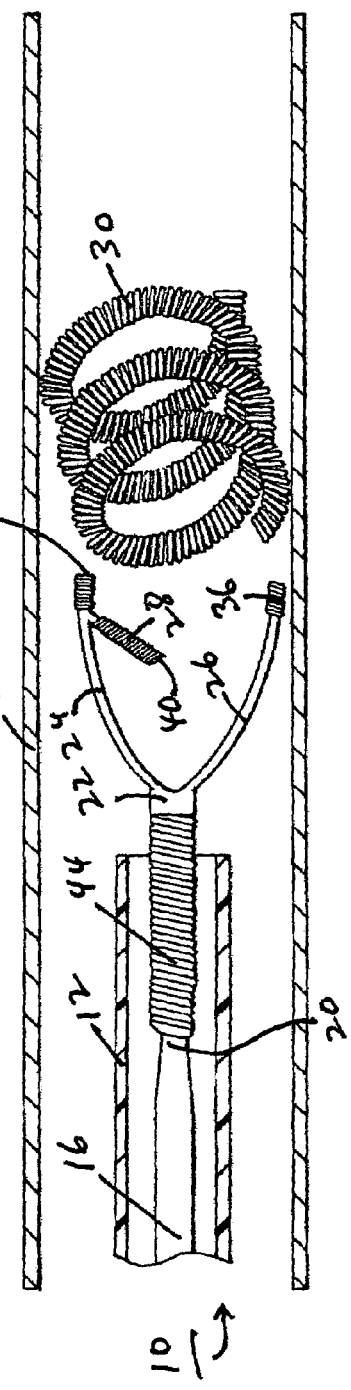
FIG. 3B is a view similar to the view of FIG. 3A, but with the arms of the embolic coil retrieval device extending distal of the catheter and being in their expanded position.

Referring to FIG. 1, an embolic coil retrieval system 10 is shown therein. System 10 includes a microcatheter 12 formed of a polymeric material as is known in the art, the proximal end 14 of which comprises a luer connector. Except for the proximal end of the microcatheter 12, the remaining portions of the microcatheter are preferably uniform. Although no limitation is intended, as a specific example, the inner diameter of the catheter is preferably between 0.010 inch and 0.025 inch, and the outer diameter of the catheter is preferably between 0.030 inch and 0.050 inch.

Positioned within microcatheter 12 is a wire device 16, which wire device 16 has pushability with respect to the catheter so that it can be manipulated like a guidewire. The proximal portion 18 of the wire device 16 is generally uniform but the wire device becomes tapered at a distal portion 20 which connects to a headpiece 22 including a pair of arms 24, 26. Proximal portion 18 of the wire device 16 is stiffer than the distal headpiece portion 22 which includes arms 24 and 26. Arm 24 carries a latch member 28 that extends at an angle with respect to the arm 24 and toward the proximal end of arm 24.

Arms 24 and 26 are collapsible and are shown in FIG. 1 in their collapsed position within the microcatheter.

Figure 4:
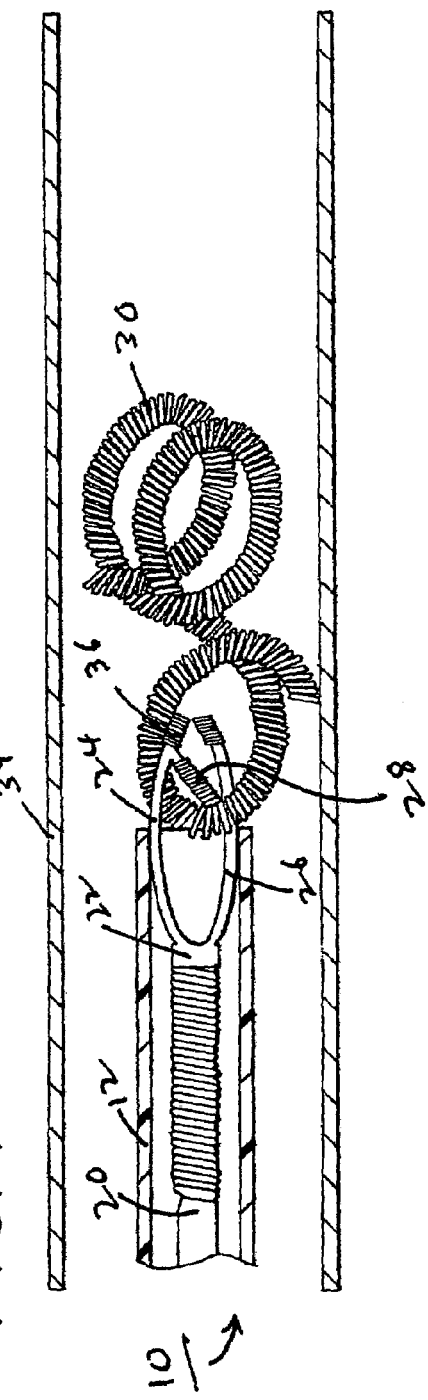
FIG. 4 is a view similar to the views of FIGS. 3A and 3B but with the latch being engaged with the embolic coil within the patient's vessel.

Although there are numerous equivalent ways in which the wire device 16 can be fabricated, as a preferred example the wire device is laser cut from a rod of nitinol measuring 0.018 inch in diameter. Nitinol is a superelastic alloy comprised of nickel and titanium. The wire device has a greater length than the length of the microcatheter so that it can be delivered through the lumen of the microcatheter to engage and retrieve an embolic coil 30 (FIGS. 3A, 3B and 4). The length of each portion of the wire device 16 varies by necessity according to the length of the vasculature to be navigated.

Although no limitation is intend, as a specific example the proximal portion 18 of the wire device 16 may have a diameter of between about 0.014 inch and 0.016 inch. The intermediate tapered portion 20 of the wire element 16 is tapered by grinding so that its diameter decreases from between about 0.014 inch and 0.016 inch to about 0.005 inch at the distal end of the tapered portion.

Although no limitation is intended, in the illustrative embodiment headpiece 22 is cut by laser from a tube of nitinol having a 0.018 inch diameter. Arms 24 and 26 are each preferably between 0.006 inch and 0.007 inch in width and between 5.0 mm and 10.0 mm in length. Latch element 28 is preferably between about 0.002 inch and 0.003 inch in width and between about 2.0 mm and 3.0 mm in length. Latch element 28 is preferably integrally struck from arm 24 as seen most clearly in FIG. 2.

Headpiece 22 is preferably attached to tapered portion 20 by soldering. Each of the arms 24, 26 has an end projection 32 that preferably is about 0.002 inch wide, although no limitation is intended. The opening range of the arms 24, 26 is preferably between 1.5 mm and 4.5 mm, depending upon the size of the vessel 34.

Projections 32 are formed at the distal end of each arm for the attachment of the radiopaque platinum marker coils 36. The diameter of these projections 32 is reduced from that of the remainder of the arms so that once the marker coils 36 are affixed, their outer diameter will be substantially the same as the outer diameter of the remainder of the arms.

A radiopaque marker coil 36 is attached to each of the projections 32 and a radiopaque marker coil 38 is attached to latch element 28. A marker coil 44 is also attached to headpiece 22, proximal of arms 24 and 26. The marker coils may be attached by soldering. Alternatively, instead of soldering marker coils the device may be radiopacified by means of electroplating or ion deposition. Further, some or all of wire device 16 may be formed from polymers such as polycarbonate or nylon or other equivalent materials.

In the construction of arms 24 and 26, a tube of nitinol is cut so that the arms are oriented opposite to each other and are arcuate in shape. The arms are heat treated while in the open configuration so that they remain outwardly biased when they are not constrained by the lumen of the catheter 12. After the arms are cut by laser from the nitinol tube, latch element 28, which may also be slightly arcuate in shape, is cut from the central portion of arm 24. Latch element 28 is heat treated while the arms are oriented in their open configuration. The latch element is angulated downward so that its distal end 40 is oriented toward a proximal portion of the opposing arm 26. Latch element 28 does not contact opposing arm 26 when the arms 24, 26 are in their open configuration.

The operation for retrieving an embolic coil using the wire device 16 is illustrated in FIGS. 3A, 3B, and 4. First, microcatheter 12 is introduced into the patient's vessel 34, to a location where the distal end 42 of microcatheter 12 is adjacent to coil 30 but at a sufficient distance therefrom so that the arms of the wire device can be extended. Wire device 16 is then introduced into the catheter and is pushed through the catheter with the arms being collapsed as illustrated in FIG. 3A. In its collapsed position, the distal end 40 of latch element 28 engages arm 26.

As illustrated in FIG. 3B, when headpiece 22 is moved to a position past the distal end of 42 of catheter 12, the arms will spring open. The physician, holding the proximal end of wire element 16, can manipulate the arms and associated latch so that it will engage coil 30 and hook onto coil 30. As illustrated in FIG. 4, the physician can then withdraw the wire element 16, which will cause the arms to collapse under the forces provided by the lumen of the microcatheter acting upon the outside surfaces of the arms. In this manner, distal end 40 of latch element 28 will engage arm 26 to secure a portion of coil 30 whereby the coil will move into the microcatheter and be withdrawn via the proximal end of the microcatheter. Although it is preferred that distal end 40 of latch element 28 engage arm 26 when the arms are collapsed, distal end 40 may be closely adjacent arm 26 instead of engaging it so long as the space between distal end 40 and arm 26 is less than the outer diameter d of the helix that forms embolic coil 30 (see FIG. 3A).

As a result of the latch construction of the present invention, the embolic coils can be engaged and latched in a manner that prevents their dislodgement once the latch is engaged. This is in contrast to prior art coil retrieval devices in which a loop is used and the physician attempts to lasso the misplaced coil. Using the present invention, the physician is provided with an easier ability to grasp a coil that may be in a loop configuration, without the coil having an opportunity to become dislodged from the retrieval device.

Although an illustrative embodiment of the invention has been shown and described, it is to be understood that various modifications and substitutions may be made by those skilled in the art without departing from the novel spirit and scope of the present invention.

The invention claimed is:

1. A method for retrieving embolic coils used for treating an aneurysm, comprising the steps of:
   providing a wire device that is pushable through a microcatheter and has a flexible distal portion comprising a distal collapsible arm with a latch member carried by the arm;
   introducing a microcatheter into the patient's vessel leading to the aneurysm;
   introducing the wire device, into the microcatheter whereby the arm collapses while it is within the microcatheter;
   pushing the distal end of the wire device through the microcatheter whereby the arm opens when it extends out of the distal end of the microcatheter;
   manipulating the latch member so that it engages an embolic coil to be retrieved; and
   withdrawing the latch-engaged embolic coil and wire device through the catheter whereby the arm becomes collapsed as the arm is withdrawn through the catheter.

2. A method as defined in claim 1, in which the flexible distal portion comprises distal collapsible arms with a latch member carried by at least one of the arms.

3. A method as defined in claim 1, in which the wire device has a stiffer proximal portion than the distal portion.

4. A method as defined claim 1, in which a portion of the collapsible arm is radiopaque.

5. A method as defined in claim 1, in which the arm and latch are formed from a composition comprising nitinol.

6. A method for retrieving embolic coils used for treating an aneurysm, comprising the steps of:

providing a wire device that is pushable through a microcatheter and has a flexible distal portion comprising a pair of distal collapsible arms with a latch member carried by at least one of the arms, the wire device having a stiffer proximal portion than the distal portion and a portion of the collapsible arm or latch being radiopaque;

introducing a microcatheter into a patient's vessel leading to the aneurysm;

introducing the wire device, into the microcatheter whereby the arms collapse while they are within the microcatheter;

pushing the distal end of the wire device through a microcatheter whereby the arms open when they extend out of the distal end of the catheter;

manipulating the latch member so that it engages an embolic coil to be retrieved; and withdrawing the latch-engaged embolic coil and wire device through the catheter whereby the arms become collapsed as the arms are withdrawn through the catheter.

* * * * *